United States Patent [19]

Beck et al.

[11] Patent Number: 5,106,618
[45] Date of Patent: Apr. 21, 1992

[54] METHOD OF TREATING PROTOZOAL GASTROINTESTINAL DISORDERS BY ADMINISTERING HYPERIMMUNE MILK PRODUCT

[75] Inventors: Lee R. Beck, Lebanon, Ohio; Donald P. Kotler, New Rochelle, N.Y.

[73] Assignee: Stolle Research and Development Corporation, Cincinnati, Ohio

[21] Appl. No.: 355,786

[22] Filed: May 22, 1989

Related U.S. Application Data

[63] Continuation of Ser. No. 69,139, Jul. 2, 1987, abandoned.

[51] Int. Cl.$^5$ .................... A61K 39/395; A61K 39/02
[52] U.S. Cl. ..................... 424/85.8; 424/86; 424/87; 424/88; 424/89; 424/92; 424/535; 514/2; 514/8; 514/12; 514/21; 530/395; 530/389.5; 530/389.1; 530/832
[58] Field of Search ............... 424/85.8, 86, 87, 93, 424/95, 101, 88, 89; 514/2, 8, 21, 10, 12; 530/387, 388, 395

[56] References Cited

U.S. PATENT DOCUMENTS

| | | |
|---|---|---|
| 3,128,230 | 4/1964 | Heinbach et al. ............... 424/92 |
| 3,553,317 | 1/1971 | Michaelson et al. ............ 424/87 |
| 3,626,057 | 12/1971 | Sarwar ............................ 424/87 |
| 3,646,193 | 2/1972 | Michhaelson et al. .......... 424/87 |
| 3,853,990 | 12/1974 | Madigan et al. ................. 424/87 |
| 3,911,108 | 10/1975 | Singh et al. ..................... 424/86 |
| 3,975,517 | 8/1976 | Wilson ............................ 424/87 |
| 3,984,539 | 10/1976 | Khouw et al. ................... 424/87 |
| 4,324,782 | 4/1982 | Beck et al. ...................... 424/87 |
| 4,377,569 | 3/1983 | Plymate .......................... 424/87 |
| 4,477,432 | 10/1984 | Hardie ............................ 424/87 |
| 4,689,221 | 8/1987 | Kiyoshige et al. .............. 424/87 |
| 4,816,563 | 3/1989 | Wilson et al. ................... 424/88 |
| 4,879,110 | 11/1989 | Beck et al. ...................... 424/88 |
| 4,919,929 | 4/1990 | Beck ............................... 424/85.8 |

FOREIGN PATENT DOCUMENTS

| | | |
|---|---|---|
| 0064103 | 11/1982 | European Pat. Off. ......... 424/87 |
| 2522999 | 12/1976 | Fed. Rep. of Germany .... 424/87 |
| 2126236 | 3/1984 | United Kingdom ............ 424/87 |

OTHER PUBLICATIONS

Pasieka et al., Can. J. Microbiol., 22, 1113–1119, (1976).
Bohl et al., Am. J. Vet. Res., 36(3), 267–271, (1973).
Saif et al., Am. J. Vet. Res., 40, 115–117, (1979).
Moon et al., Am. J. Fet. Res., 44(3), 493–496, (1983).
Loeffler et al., Am. J. Vet. Res., 46(8), 1728–1732, (Aug. 1985).
Opdebeeck et al., Am. J. Vet. Res., 46(7), 1561–1569, (1985).
Tzipori, S. et al., Brit. Med. J. 293:1276–1277 (1986).
Kotler, D. P., Abstract Presented at the III International Conference on Acquired Immunodeficiency Syndrome (AIDS) on Jun. 1–5, 1987, Washington, D.C.

*Primary Examiner*—John Doll
*Assistant Examiner*—Lila Feisee
*Attorney, Agent, or Firm*—Sterne, Kessler, Goldstein & Fox

[57] ABSTRACT

The invention comprises treatment of gastrointestinal disorders of parasitic protozoan and bacterial origin in immunocompromised and immunocompetent animals by administration hyperimmune milk products.

21 Claims, No Drawings

METHOD OF TREATING PROTOZOAL GASTROINTESTINAL DISORDERS BY ADMINISTERING HYPERIMMUNE MILK PRODUCT

This application is a continuation of application Ser. No. 07/069,139, filed Jul. 2, 1987, now abandoned.

BACKGROUND OF THE INVENTION

1. Field of the Invention

The present invention relates to a method for the treatment of disorders of the gastrointestinal tract, such as result from immunodeficiency states.

2. Description of the Background Art

Immunologic functions are mediated by two developmentally independent, but functionally interacting, families of lymphocytes. The activities of B and T lymphocytes and their products in host defense are closely integrated with the functions of other cells of the reticuloendothelial systems, such as macrophages and polymorphonuclear leukocytes, as well as with basophils and tissue mast cells.

Immunodeficiency syndromes, whether congenital, spontaneously acquired, or iatrogenic, are characterized by unusual susceptibility to infections and, sometimes, to autoimmune disease and to lymphoreticular malignancies. The types of infection often provide the first clue to the nature of the immunologic defect.

Patients with defects of humoral immunity have recurrent or chronic sinopulmonary infection, meningitis, and bacteremia, most commonly caused by pyrogenic bacteria such as *Hemophilus influenziae, Streptococcus pneumoniae*, and *Staphylococci*. Lawton, A.R., et al., Immune Deficiency Diseases, in Petersdorf, R.G., et al., eds., *Harrison's Principles of Internal Medicine*, 10th ed., 1983, p. 354.

Abnormalities of cell-mediated immunity predispose to disseminated viral infections, particularly with latent viruses such as herpes, varicella zoster, and cytomegalo-virus. Patients so affected also almost invariably develop mucocutaneous conditions, and frequently acquire widely disseminated fungal infections. Id at 355.

The most severe form of immune deficiency occurs in individuals, often infants, who lack both humoral and cell-mediated immune functions. They are susceptible to the whole range of infectious agents, including organisms not ordinary considered pathogenic. Multiple infections with viruses, bacteria, fungi and protozoa occur, often simultaneously.

The acquired immunodeficiency syndrome (AIDS) is a disease that has been recognized since 1981. It is characterized by severe acquired immunodeficiency, affecting certain recognized risk groups—homosexual or bisexual males (71%), intravenous drug users (17%), patients with no admitted history of homosexuality or intravenous drug abuse (5%), and hemophiliacs (1%). Cases of AIDS have been described in infants of mothers with AIDS or at risk for AIDS, and fewer than 6% of patients fall into no apparent risk group. Bellanti, J.A., ed., *Immunology III*, Saunders, Phila., 1985, 503. AIDS is the most severe manifestation of chronic infection by human immunodeficiency virus (HIV), which attacks T-helper/inducer lymphocytes.

Full-blown AIDS is characterized by opportunistic infections with or without unusual neoplasms such as Koposi's sarcoma. The most common (63% of AIDS population) opportunistic infection is *Pneumocystis carinii* pneumonia; it is seen in the absence of Koposi's sarcoma in 50% of AIDS patients, and together with this sarcoma in an additional 8% of patients. Occasionally, HIV infection presents as an acute mononucleosis-like illness, with fever, malaise, myalgias, arthralgias, headache, nausea, severe diarrhea, and lymphoadenopathy. Wetherbee, R.E., *Laboratory Medicine* 17:679-684 (1986). Among the other opportunistic infections seen in AIDS patients are: *Mycobacterium avium intracellulare, Cryptococcus neoformens* meningitis, *Candida albicans* esophagitis and thrush, progressive herpes simplex viral infection of the mucocutaneous area, *Toxoplasma gandii* infection (particularly of the central nervous system) and cryptosporidiosis. Bellanti, supra, at 504.

Cryptosporidiosis, which has been seen in at least 5% of AIDS patients (Wetherbee, supra, at 680), is caused by the coccidian protozoa parasite, Cryptosporidium. This newly recognized human pathogen is associated with severe enteritis and, perhaps, cholecystitis in immunocompromised patients, particularly those with AIDS. The same organism is also associated with significant, although self-limited, diarrheal illness in the immunocompetent host. The number of reported cases of cryptosporidiosis is continually increasing since it was first described in 1976, as more physicians become aware of the disease and microbiologists learn to identify the parasite Soave, R. et al., *Controversies in the Diagnosis and Management of Infectious Diseases*, 1986, pp. 1012-1022. Cryptosporidia appear to invade the microvillus border of gastrointestinal epithelial cells, and have been implicated in enteritis in animals as well as in humans.

The organism is capable of crossing species barriers. Indeed, it has been reported that immunocompetent persons who have been in contact with the feces of Cryptosporidia-infected farm animals with diarrhea, may themselves become infected with this protozoan parasite, and may present with the classical symptoms of malaise, nausea, headache, abdominal cramps, and diarrhea. Current, W.L., et al., *New England Journal of Medicine* 308:1252-1257 (1983).

Instances of person-to-person transmission of symptomatic infection have also been reported, occurring in both the community and hospital settings. Wetherbee, supra, at 680.

In patients with or without risk for AIDS, cytosporidiosis occurs with a severity and duration apparently proportional to the degree of immunocompromise in the patient. Symptoms of cryptosporidiosis include abdominal pain, nausea, vomiting, and intermittent watery diarrhea without blood or mucus. Fever may or may not be present, but weight loss is significant in most cases. Diagnosis of cryptosporidiosis may often be missed. For example, the chronic diarrhea, prolonged fever, extreme weight loss, anorexia, and severe infection, in a group of AIDS patients, was referred to as "unexplained." Malebranche, R. et al., *Lancet* 873-877 (October 15, 1983). It is likely that these symptoms were due to undiagnosed cryptosporidiosis. Diagnosis of cryptosporidiosis is achieved through identification of Cryptosporidia oocysts in the stool, as the spherical organisms are sloughed off from the intestinal atrophic microvillus border tissue.

There is currently no known effective therapy for cryptosporidial infection. Although the immunocompetent host usually has a self-limited illness, there have been reports of severe enteritis requiring hospitalization of these patients. Efficacious anti-cryptosporidial therapy could be useful in decreasing morbidity as well as the length of time oocyst shedding occurs in the immunocompetent host infected with Cryptosporidia. In the immunocompromised patient, such as those suffering with AIDS, cryptosporidiosis is usually persistent, and causes significant malnutrition and morbidity. Current treatment is limited to symptomatic support through parenteral fluid, electrplyte, trace element, and nutrition repletion, as well as administration of antisecretory and anti-peristaltic pharmaceuticals. Wetherbee, supra, at 681.

For the immunocompromised host, the need for efficacious therapy is more pronounced than for the immunocompetent individual. A vast array of antimicrobial, immunomodulatory and nonspecific anti-diarrheal drugs, as well as special diets, have been administered to such patients. With few exceptions, attempts at therapeutic intervention have met with failure, both in the control of enteric symptoms and in the eradication of the parasite. Soave et al, supra, at 1012.

An important need exists, therefore, for an effective method for both preventing and treating disorders due to parasitic protozoa such as Cryptosporidia.

*Isospora belli*, a related parasitic protozoa, can cause a similar syndrome in patients with AIDS; an incidence of 15% in AIDS patients has been reported. DeHovitz et al., *New England Journal of Medicine*, 315:87-90 (1986). Although isosporiasis responds to therapy with trimethoprim-sulfamethoxazole, it is associated with an extremely high rate of recurrence.

It has been known in the prior art to produce milk having a variety of therapeutic effects. Beck, for example, has disclosed a milk containing antibody to *Streptococcus mutants* which has a dental caries inhibiting effect (Beck, U.S. Pat. No. 4,324,784). The milk is obtained by hyper-immunizing a cow with *Streptococcus mutans* antigen and obtaining the therapeutic milk therefrom. Beck has also described a milk having anti-arthritic properties (co-pending U.S. application Ser. No. 875,140, filed Feb. 6, 1978) and has described and patented a milk having anti-inflammatory properties (U.S. Pat. No. 4,284,623). Heinbach (U.S. Pat. No. 3,128,230), has described and patented a cow milk having alpha, beta, and gamma globulins against anti-9-enic haptens. Singh (U.S. Pat. No. 3,911,108), Peterson (U.S. Pat. No. 3,376,198 and Canadian Pat. No. 587,849), Holm (U.S. application (published) Ser. No. 628,987), and Tunnak et al. (Great Britain Patent No. 1,211,876), have also described antibody-containing milks.

None of these aforementioned references, however, disclose or suggest milk having anti-infective properties against gastrointestinal microbial pathogens.

SUMMARY OF THE INVENTION

The present invention is based upon the inventor's consideration that hyperimmune milk product would be useful to treat gastrointestinal disorders caused by pathogenic microorganisms.

With this in mind, the present inventors administered such hyperimmune product to human patients suffering from acquired immunodeficiency syndrome for the purpose of treating gastrointestinal disorders related to the disease.

Further investigations demonstrated that these patients presented with the symptoms of infection with the gastrointestinal protozoan parasite, Crypotosporidium, namely, cryptosporidiosis and that the hyperimmune product exerted an anti-Cryptospordia effect and alleviated the clinical symptoms of cryptosporidiosis.

Accordingly, the present invention is the discovery that hyperimmune milk product, found in milk from milk-producing animals hyperimmunized against particular polyvalent bacterial antigens, is effective against pathogenic parasitic protozoa that inhabit the gastrointestinal tract of humans, when the hyperimmune milk product is administered in an amount sufficient to produce anti-infective effects. This discovery is particularly surprising in view of the fact that the polyvalent vaccine does not contain antigen corresponding to the particular parasitic protozoa.

DETAILED DESCRIPTION OF THE PREFERRED EMBODIMENTS

The invention comprises administration of hyperimmune milk product to an animal for the purpose of treating gastrointestinal disorders.

By the term "hyperimmune milk product" is intended milk product obtained from hyperimmune milk-producing animals. By the term "hyperimmune milk" is intended, for the purpose of this invention, milk obtained from animals maintained in a hyperimmune state, the details for hyperimmunization being described in greater detail below.

By the term "milk product" is intended, for the purposes of the present invention, whole milk, whole milk fractions, and derivatives of whole milk, which contain the biologically active component resulting from the hyperimmunization of the milk-producing animal. Thus the term includes whole milk, skim milk, powdered milk, milk antibodies, and fractions of the antibodies.

By the term "milk-producing animal" is intended, for the purpose of this invention, mammals that produce milk in commercially feasible quantities, preferably cows, sheep and goats, more preferably dairy cows of the genus Bos (bovid), particularly those breeds giving the highest yields of milk, such as Holstein.

By the term "gastrointestinal disorder" is intended, for the purpose of this invention, infections relating to the stomach and intestine of a mammal that result in a disturbance of function, structure, or both.

By the term "treating" is intended, that the symptoms of the disorder and/or pathogenic origin of the disorder be ameliorated or completely eliminated.

By the term "administer" is intended, for the purpose of this invention, any method of treating a subject with a substance, such as orally, intranasally, parenterally (intravenously, intramuscularly, or subcutaneously) or rectally.

By the term "animal" is intended, for the purpose of this invention, any living creature that is subject to gastrointestinal disorders, including humans, farm animals, domestic animals, or zoological garden animals.

Examples of gastrointestinal disorders that may be treated with the milk product of the present invention include enteritis and similar disorders that result from infection with gastrointestinal microbes, including but not limited to the parasitic protozoa Cryptosporidia (cryptosporidiosis) and *Isospora belli* (isosporiasis).

The hyperimmune milk product of the present invention can be used in the treatment of opportunistic gastrointestinal infections in immunocompromised individuals. Further, the milk product may be used to treat immunocompetent individuals who are exposed to such pathogenic organisms.

As the milk antibodies are raised against a wide variety of bacterial antigens, including bacteria which normally are found in the gastrointestinal tract of humans and other mammals and which can be pathogenic in immunocompromised patients (Harrison's, supra, at 854), said milk antibody are also useful in treating gastrointestinal disorders of bacterial origin.

The invention is based in part on the discovery that when a milk-producing animal is brought to a specific state of hyperimmunization, the bovid will produce milk which has the highly beneficial property not only of suppressing the symptoms in man and other mammals of infection with gastrointestinal parasitic protozoa, but also of being protozoacidal in such hosts. The beneficial properties are not produced by all bovids that are immunized. Further, the induction of immune sensitivity alone is insufficient to cause the appearance of the properties in milk, as is shown by the fact that normal cows' milk does not contain these properties, even though cows have become sensitized against various antigens during normal immunization against cow diseases and during normal exposure to the environment.

Furthermore, the milk factor(s) is(are) not always produced by bovids maintained in the immune state. It is only in specific hyperimmune states that the milk has the desired primary effects. This special state may be achieved by administering an initial immunization followed by periodic boosters with sufficiently high doses of specific antigen(s). The preferred dosage of booster should be equal to or greater than 50% of the dosage necessary to produce primary immunization of the bovid. Thus, there is a threshold booster dosage below which the properties are not produced in the milk, even though the cow is in what normally one would call an immune state. In order to achieve the requisite hyperimmune state, it is essential to test the hyperimmune milk after a first series of booster administrations. If the beneficial factors are not present in the milk, additional boosters of higher dosage are administered until the properties appear in the milk.

In summary, one process of producing the beneficial hyperimmune milk product comprises the following steps:

1. Antigen selection;
2. Primary immunization of the bovid;
3. Testing the serum to confirm sensitivity induction;
4. Hyperimmunization with boosters of appropriate dosage; and, optionally,
5. Testing the milk for beneficial properties.
6. Collecting the milk from the hyperimmune bovid.
7. Processing the milk to isolate the beneficial factor(s).

Step 1: Any antigens or combination of antigens may be employed. The antigens can be bacterial, viral, protozoan, fungal, cellular, or any other substances to which the immune system of a bovid will respond. The critical point in this step is that the antigen(s) must be capable, not only of inducing immune and hyperimmune states in the bovid, but also of producing the beneficial antibodies or other factors in the milk. Preferably, polyvalent bacterial antigens are used. One preferred vaccine is a mixture of polyvalent bacterial antigens, referred to as Series 100 vaccine in copending U.S. Ser. No. 910,297, filed Sep. 17, 1986, a File Wrapper Continuation of U.S. patent application Ser. No. 576,001, which is incorporated herein by reference to the extent that it provides details of the vaccine used in the present invention.

Step 2: The antigen(s) can be administered in any method that causes sensitization. In one method, a vaccine composed of antigen derived from $1 \times 10^6$ to $1 \times 10^{20}$, preferably $10^8$ to $10^{10}$, most preferably $2 \times 10^8$, heat-killed bacteria is administered by intramuscular injection. However, other methods such as intravenous injection, intraperitoneal injection, rectal suppository, or oral administration may be used.

Step 3: It is necessary to determine whether or not the cow has become sensitive to the antigen. There are a number of methods known to those skilled in the art of immunology to test for sensitivity (*Methods in Immunology and Immunochemistry*, William, C.A., and Chase, W.M., Academic Press, New York, vols. 1–5 (1975)). The preferred method is to use a polyvalent vaccine comprising multiple bacterial species as the antigen and to test for the presence of agglutinating antibodies in the serum of the cow before and after challenge with the vaccine. The appearance of milk antibodies after immunization with the vaccine indicates sensitivity; at this point it is possible to proceed to step 4.

Step 4: This involves the induction and maintenance of the hyperimmune state in the sensitized bovid. This is accomplished by repeated booster administration at fixed time intervals of the same polyvalent vaccine that was used to achieve the primary sensitization. A two-week booster interval is optimal for polyvalent bacterial antigens. However, it is necessary to ensure that the animal does not pass from a hyperimmune state to a state of immune tolerance to the antigen.

In an alternative embodiment, it is also possible to combine different immunization procedures, e.g., simultaneously administering encapsulated and liquid antigen, or intramuscular injection for primary immunization, and booster doses by oral administration or parenteral administration by microencapsulation means. Many different combinations of primary and hyperimmunization are known to those skilled in the art.

Step 5: It is necessary to test the beneficial effects of the milk. This can be accomplished by any research technique that tests the effects of either the hyperimmune milk or products derived therefrom upon either the parasitic protozoa itself or on the symptoms of infection by such organisms in test subjects (e.g., mammals infected by parasitic protozoa or immunocompromised human patients).

Step 6: This involves the collection and processing of the milk. The milk can be collected by conventional methods; however, special processing is necessary to protect the beneficial properties of the milk. The beneficial properties of the milk are heat sensitive. Accordingly, in order to prevent denaturation of milk proteins by heat, it is preferable to pasteurize the milk at low temperature under reduced pressure.

The pasteurized hyperimmune milk can be used in various forms. It can be used in the form of a milk powder produced by conventional spray-drying techniques, following concentration of defatted milk under vacuum at low temperatures. (See, e.g., Kosikowski, F., "Cheese and Fermented Milk Products," 2nd ed., 1977), as long as the milk powder retains the beneficial properties.

Fluid milk can also be used, as well as concentrated milk products or fractions of the milk containing the biologically active factor or factors.

It is preferred to use a lactose-free milk antibody concentrate, in contrast to whole milk or skim milk powder, for certain types of patients; many AIDS patients cannot tolerate the lactose in milk. The preferred embodiment of the invention is a milk antibody concentrate prepared by ultrafiltration of the pasteurized, concentrated hyperimmune milk through a membrane that retards molecules greater than 100,000 molecular weight; immunoglobulins have molecular weights greater than 100,000. The use of ultrafiltration to concentrate proteins out of fluids is well known to the art. It is preferred to concentrate the milk proteins 10-to-100 fold, most preferably 30-fold.

In a preferred embodiment, hyperimmunization may be achieved by a single administration of microencapsulated vaccine such as the microencapsulated bacterial vaccine described in co-pending U.S. application Ser. No. 910,297, filed Sep. 17, 1986, a File Wrapper Continuation of U.S. patent application Ser. No. 576,001, which is incorporated herein by reference in its entirety and which provides details of the formulations of antigen-containing shaped matrix materials. Generally, the antigen-containing shaped matrix materials are formed from polymers of biocompatible material, preferably biodegradable or bioerodable materials, preferably polylactic acid, polyglycolic acid, copolymers of lactic and glycolic acids, polycaprolactone, copolyoxalates, proteins such as collagen, fatty acid esters of glycerol, and cellulose esters. These polymers are well known in the art and are described, for example, in U.S. Pat. Nos. 3,773,919; 3,887,699; 4,118,470; 4,076,798, all incorporated by reference herein. Heat-killed bacterial antigens are encapsulated in such matrix materials, preferably as microspheres of between 1 and 500 microns diameter, preferably 10 to 200 microns. The encapsulation processes are conventional and comprise phase separation methods, interfacial reactions, and physical methods. Many combinations of matrices and many concentrations of assorted antigens may be employed, in order to provide for optimal rates of release of bacterial antigens to the host body from the microparticles. These combinations can be determined by those skilled in the art without undue experimentation.

The invention is based in part upon the unexpected discovery that hyperimmune milk product, produced by hyperimmunizing a milk-producing animal against a polyvalent bacterial vaccine, is effective in treating chronic cryptosporidiosis in AIDS patients. The parasitic protozoa Cryptosporidium is not included in the vaccine used to hyperimmunize the animal. It is surprising, therefore, that treatment with milk product, obtained from animals immunized against a mixed bacterial antigen vaccine, is effective in killing such intestinal parasitic protozoa and in alleviating the profound diarrhea that accompanies cryptosporidiosis.

Having now generally described this invention, the same will be further described by reference to certain specific examples which are provided herein for purposes of illustration only, and are not intended to be limiting unless otherwise specified.

PREPARATION OF MILKS

The following protocol also appears in U.S. Ser. No. 910,297, filed Sep. 17, 1986 a co-pending File Wrapper Continuation Application of U.S. patent application Ser. No. 576,001, which is herein incorporated in its entirety by reference.

EXAMPLE 1A

Preparation of S-100 Vaccine

A bacterial culture containing the spectrum of bacteria shown in Table 1 below as obtained from the American Type Culture Collection was reconstituted with 15 ml of media and incubated overnight at 37° C. Once good growth was obtained, approximately one-half of the bacterial suspension was employed to inoculate one liter of broth with the inoculate being incubated at 37° C. The remaining suspension was transferred to sterile glycol tubes and stored at −20° C. for up to six months.

After good growth was visible in the culture, the bacterial cells were harvested by centrifugation of the suspension for 20 minutes to remove the media. The bacterial pellet obtained was resuspended in sterile saline solution and the bacterial sample was centrifuged three times to wash the media from the cells. After the third sterile saline wash, the bacterial pellet obtained upon centrifugation was resuspended in a small amount of double distilled water.

The media-free bacterial suspension was heat-killed by placing the suspension in a glass flask in an 80° C. water bath overnight. The viability of the broth culture was tested with a small amount of heat-killed bacteria. Broth was inoculated with heat-killed bacteria, incubated at 37° C. for five days and checked daily for growth, as the bacteria have to be killed for use in the vaccine.

The heat-killed bacteria were lyophilized until dry. The dry bacteria were then mixed with sterile saline solution to a concentration of $2.2 \times 10^8$ bacterial cells/ml saline (1.0 optical density reading at 660 nm).

TABLE 1

| S-100 Bacteria List | | | |
|---|---|---|---|
| Name | Media | Gram + or − | ATTC # |
| 1. Staph. aureus | BHI | + | 11631 |
| 2. Staph. epidermidis | BHI | + | 155 |
| 3. Strep. pyogenes, A. Type 1 | APT | + | 8671 |
| 4. Strep. pyogenes, A. Type 3 | APT | + | 10389 |
| 5. Strep. pyogenes, A. Type 5 | APT | + | 12347 |
| 6. Strep. pyogenes, A. Type 8 | APT | + | 12349 |
| 7. Strep. pyogenes, A. Type 12 | APT | + | 11434 |
| 8. Strep. pyogenes, A. Type 14 | APT | + | 12972 |
| 9. Strep. pyogenes, A. Type 18 | APT | + | 12357 |
| 10. Strep. pyogenes, A. Type 22 | APT | + | 10403 |
| 11. Aerobacter aerogenes | BHI | − | 884 |
| 12. Escherichia coli | BHI | − | 26 |
| 13. Salmonella enteritidis | BHI | − | 13076 |
| 14. Pseudomonas aeruginosa | BHI | − | 7700 |
| 15. Klebsiella pneumoniae | BHI | − | 9590 |
| 16. Salmonella typhimurium | BHI | − | 13311 |
| 17. Haemophilus typhimurium | BHI | − | 9333 |
| 18. Strep. mitis | APT | + | 6249 |
| 19. Proteus vulgaris | BHI | − | 13315 |
| 20. Shigella dysenteriae | BHI | − | 11835 |
| 21. Diplococcus pneumoniae | APT | + | 6303 |
| 22. Propionibacter acnes Actinomyces (anaerobe) | Broth | + | 11827 |
| 23. Strep. sanguis | APT | + | 10556 |
| 24. Strep. salivarius | APT | + | 13419 |
| 25. Strep. mutans | BHI | + | 25175 |
| 26. Strep. agalactiae | APT | + | 13813 |

Cows were given daily injections of 5 ml samples of the polyvalent liquid vaccine. Antibody (IgG) titer levels for the injected cattle were determined periodically. The antibody (IgG) titer levels were determined by taking optical density readings at 410 nm of antibody containing fluid samples obtained from cow's milk.

EXAMPLE 1B Heat-killed bacteria were prepared in the manner described above. The polyvalent antigen sample (S-100) obtained was microencapsulated by a conventional phase-separation process to prepare a polyvalent antigen-containing microparticle product, the process being described in copending U.S. application Ser. No. 910,297, filed Sep. 17, 1986, which is File Wrapper Continuation application to U.S. patent application Ser. No. 576,001. The polymeric matrix material employed was a biodegradable lactide-glycolide copolymer. The microparticles were less than 250 microns in diameter. Approximately 750 mg of microparticles containing 22% (16.5 mg) of polyvalent antigen was then suspended in about 3 cc of a vehicle (1 wt. % Tween 20 and 2 wt. % carboxymethyl cellulose in water).

A small group of cattle was selected from a larger herd of cattle. Five of these randomly selected cattle were selected as controls. Four cattle were treated by an injection of microparticle-containing solution prepared as described above.

The four cows were injected intramuscularly with the polyvalent antigen containing microparticles. Microparticle samples BO22-41-1 and BO22-41-2 were sterilized with 2.0 mRad of gamma radiation, while samples BO22-41-3 and BO22-41-4 were unsterilized. Antibody (IgG) titer levels were determined periodically from samples of cows' milk obtained from the inoculated cows, as well as from the control cows.

EXAMPLE 2

Materials and Methods

Cows' milk immunoglobulins were prepared from the milk of cows that had been hyperimmunized with human enteric bacterial antigens (but not Cryptosporidium) using a micro-encapsulated, slow-release vaccine described supra.

The milk was pasteurized at low temperature under reduced pressure to prevent denaturation, then passed through a molecular sieve designed to retard molecules greater than $M_r = 100,000$. The retarded molecules, which include milk immunoglobulins (molecular weights of all immunoglobulins are greater than 150,000), were concentrated about 30-fold.

EFFECTS ON HUMAN PATIENTS

EXAMPLE 3

Four AIDS patients were treated. All had diarrhea with cryptosporidia in stool samples and infection was confirmed on tissue biopsy in three patients. The patients were treated with increasing oral doses of milk immunoglobulin concentrate (Example 2), following the ingestion of 15 gr of sodium bicarbonate, 4 times per day. Generally, treatment with hyperimmune milk product comprised a daily dosage level of from 40 to 100 gms of protein administered in four equal parts. Three of the four patients responded favorably, with reappearance of some or all formed stools, in contrast to copious watery diarrhea prior to treatment. In three patients treatment resulted in the disappearance of cryptosporidial oocysts from their stools, and the parasite disappeared from intestinal biopsies in two of the three patients tested. The fourth patient had severe small intestinal infestation; he did not respond clinically or by biopsy, however, he was unable to tolerate much of the mild product due to recurrent vomiting. In addition, infestation of bile ducts and gall bladder was strongly suspected in this patient due to recurrent attacks of acalculous cholecystitis.

The results strongly suggest that a large molecular weight fraction in hyperimmunized cow's milk effectively suppress cryptosporidiosis in patients with AIDS.

Having now generally described this invention, it will become readily apparent to those skilled in the art that many changes and modifications can be made thereto without affecting the spirit or scope thereof.

What is new and claimed as intended to be covered by Letters Patent of the United States is:

1. A method of treating cryptosporidiosis or isosporiasis in an immunocompromised animal which comprises:
   administering to said immunocompromised animal a hyperimmune milk product containing a biologically active component which reduces the number of oocysts in the stool, reduces the number of Cryptosporidia or Isospora parasites in the intestine or alleviates the symptoms of cryptosporidiosis or isosporiasis in a subject infected with Cryptosporidia or Isospora from a hyperimmunized milk-producing mammal selected from the group consisting of cows, sheep, and goats, in amounts sufficient to treat said cryptosporidiosis or isosporiasis, wherein said hyperimmune milk product is selected from the group consisting of hyperimmune whole milk, hyperimmune whole milk fractions, and derivatives of hyperimmune whole milk which contain said biologically active component and is prepared by a process comprising:
   (i) hyperimmunizing said milk-producing mammal with a mixture of non-protozoan bacterial antigens;
   (ii) collecting milk from said milk-producing mammal after said milk-producing mammal reaches a hyperimmune state;
   (iii) filtering said milk through a molecular sieve which excludes proteins of molecular weight greater than 100,000 daltons; and
   (iv) testing the retentate of step (iii) for its ability to reduce the number of oocysts in the stool, reduce the number of Cryptosporidia or Isospora parasites in the intestine or alleviate symptoms of cryptosporidiosis or isosporiasis in a subject infected with Cryptosporidia or Isospora by administering to said subject the retentate of step (iii) and measuring the reduction of said oocysts, parasites, or symptoms.

2. A method of treating cryptosporidiosis or isosporiasis in an AIDS patient which comprises:
   orally administering to said AIDS patient a hyperimmune milk product from a hyperimmunized milk-producing bovid in amounts sufficient to treat said cryptosporidiosis or isosporiasis, wherein said hyperimmune milk product is prepared by a process comprising
   i. intramuscularly hyperimmunizing said bovid with an injection of a microencapsulated slow-release vaccine wherein said vaccine comprises a mixture of nonprotozoan bacterial antigens selected from the group consisting of *Staphylococcus aureus; Staphylococcus epidermidis; Streptococcus pyogenes,* A. Type 1; *Streptococcus pyogenes,* A. Type 3; *Streptococcus pyogenes,* A. Type 5; *Streptococcus pyogenes,* A. Type 8; *Streptococcus pyogenes,* A. Type 12; *Streptococcus pyogenes,* A. Type 14; *Streptococcus pyogenes,* A. Type 18; *Streptococcus pyogenes,* A.

Type 22; *Aerobacter aerogenes; Escherichia coli; Pseudomonas aeruginosa; Klebsiella pneumoniae; Salmonella typhimurium; Haemophilus influenzae; Streptococcus mitis; Proteus vulgaris; Shigella dysenteriae; Diplococcus pneumoniae; Proprionibacter acnes Actinomyces* (anaerobe); *Streptococcus mutans;* and *Streptococcus agalactiae;* ii. collecting the milk from said bovid after said bovid reaches a hyperimmune state;

iii. pasteurizing said collected milk under low temperature at reduced pressure;

iv. removing the fat from said pasteurized milk;

v. filtering said defatted milk through molecular sieves which excludes proteins of molecular weight greater than 100,000; and vi. concentrating the milk proteins in the retentate of said sieve approximately 30-fold prior to administration to said AIDS patient.

3. The method of claim 1 wherein said immunocompromised animal is a human.

4. The method of claim 3 wherein said human comprises a human with acquired immunodeficiency syndrome.

5. The method of claim 1 wherein said hyperimmune milk product is in fluid form.

6. The method of claim 1 wherein said hyperimmune milk product is in solid form.

7. The method of claim 1 wherein said hyperimmune milk product is in concentrated form.

8. The method of claim 1 wherein after said collecting and prior to said filtering, said hyperimmune milk product is prepared by a process which comprises:

(i) pasteurizing said collected milk under low temperature at reduced pressure;

(ii) removing the fat from said milk.

9. The method of claim 8 wherein said retentate is concentrated greater than 10-fold.

10. The method of claim 1 wherein said milk-producing mammal is a bovid.

11. The method of claim 1 wherein said milk-producing animal is hyperimmunized by administration of a mixture of bacterial antigens comprising *Stapholococcus aureus; Stapholccocus epidermidis; Streptococcus pyogenes,* A Type 1; *Streptococcus pyogenes,* A. Type 3; *Streptococcus pyogenes,* A. Type 5; *Streptococcus pyogenes,* A. Type 8; *Streptococcus pyogenes,* A. Type 12; *Streptococcus pyogenes,* A. Type 14; *Streptococcus pyogenes,* A. Type 18; *Streptococcus pyogenes,* A. Type 22; *Aerobacter aerogenes; Escherichia coli; Pseudomonas aeruginosa; Klebsiella pneumoniae; Salmonella typhimurium: Haemophilus influenzae; Streptococcus mitis; Proteus vulgaris: Shigella dysenteriae: Diplococcus pneumoniae; Proprionibacter acnes Actinomyces* (anaerobe); *Streptococcus mutans;* and *Streptococcus agalactiae.*

12. The method of claim 1 wherein said bacterial antigen is administered to said animal orally.

13. The method of claim 12 wherein said oral dose comprises $10^6$ to $10^{20}$ cells.

14. The method of claim 1 wherein said bacterial antigen is administered parenterally.

15. The method of claim 1 wherein said bacterial antigen is administered by parenteral route in liquid form.

16. The method of claim 1 wherein said bacterial antigen is administered by parenteral route in microencapsulated form.

17. The method of claim 1 wherein said hyperimmune milk product is administered periodically to said subject.

18. The method of claim 7 wherein said periodic administration is by oral means.

19. The method of claim 17 wherein said periodic administration is by parenteral means.

20. The method of claim 17 wherein said periodic administration is by intranasal means.

21. The method of claim 17 wherein said periodic administration is by rectal means.

* * * * *